(12) United States Patent
Vidal et al.

(10) Patent No.: US 7,001,436 B2
(45) Date of Patent: Feb. 21, 2006

(54) DYEING COMPOSITION FOR KERATINOUS FIBRES COMPRISING A PARTICULAR DICATIONIC DIAZO DYE

(75) Inventors: Laurent Vidal, Paris (FR); Hervé David, Joinville le Pont (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/480,202

(22) PCT Filed: Jun. 10, 2002

(86) PCT No.: PCT/FR02/01980

§ 371 (c)(1),
(2), (4) Date: Jul. 28, 2004

(87) PCT Pub. No.: WO02/100834

PCT Pub. Date: Dec. 19, 2002

(65) Prior Publication Data

US 2004/0244123 A1    Dec. 9, 2004

(30) Foreign Application Priority Data

Jun. 11, 2001 (FR) .................................. 01 07613

(51) Int. Cl.
*A61K 7/13* (2006.01)

(52) U.S. Cl. ................. 8/405; 8/407; 8/411; 8/437; 8/451; 8/463; 8/466; 8/570; 8/573; 8/574; 548/318.1; 548/321; 548/400; 546/184; 546/249

(58) Field of Classification Search ............ 8/405, 8/407, 437, 451, 411, 463, 466, 570, 573, 8/574; 548/318.1, 321, 400; 546/184, 249
See application file for complete search history.

(56) References Cited

U.S. PATENT DOCUMENTS

| | | | |
|---|---|---|---|
| 3,271,383 A | 9/1966 | Yamaya et al. | 260/158 |
| 3,291,788 A | 12/1966 | Yamaya et al. | 260/157 |
| 3,578,387 A | 5/1971 | Zviak et al | 8/10.1 |
| 4,003,699 A | 1/1977 | Rose et al. | 8/10.2 |
| 5,061,289 A | 10/1991 | Clausen et al. | 8/405 |
| 5,380,340 A | 1/1995 | Neunhoeffer et al. | 8/409 |
| 5,534,267 A | 7/1996 | Neunhoeffer et al. | 424/70.1 |
| 5,663,366 A | 9/1997 | Neunhoeffer et al. | 548/371.4 |
| 5,708,151 A * | 1/1998 | Mockli | 534/608 |
| 5,766,576 A | 6/1998 | Löwe et al. | 424/62 |
| 5,980,587 A | 11/1999 | Samain | 8/426 |
| 6,099,592 A | 8/2000 | Vidal et al. | 8/409 |
| 6,284,003 B1 | 9/2001 | Rose et al. | 8/412 |

FOREIGN PATENT DOCUMENTS

| | | |
|---|---|---|
| DE | 23 59 399 | 6/1975 |
| DE | 3 843 892 | 6/1990 |
| DE | 41 28 490 | 3/1993 |
| DE | 41 33 957 | 4/1993 |
| DE | 42 20 388 | 12/1993 |
| DE | 195 43 988 | 5/1997 |
| EP | 0 714 954 | 6/1996 |
| EP | 0 757 083 | 2/1997 |
| EP | 0 770 375 | 5/1997 |
| FR | 1584965 | 1/1970 |
| FR | 2733 749 | 11/1996 |
| FR | 2 741 798 | 6/1997 |
| GB | 1026978 | 4/1966 |
| GB | 1153196 | 5/1969 |
| GB | 1186753 | 4/1970 |
| JP | 55-22638 | 2/1980 |
| JP | 2019576 | 1/1990 |
| JP | 5 163 124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |

OTHER PUBLICATIONS

English language Derwent Abstract of DE 41 28 490, Mar. 4, 1993.
English language Derwent Abstract of DE 42 20 388, Dec. 23, 1993.
English language Derwent Abstract of EP 0 757 083, Feb. 5, 1997.
English language Derwent Abstract of Non-English language EP 0 757 083 (attached to EP 0 757 083).
English language Derwent Abstract of Non-English language EP 0 770 375 (attached to EP 0 770 375).
English language Derwent Abstract of Non-English language JP 2019576 (attached to 2019576).
English language Derwent Abstract of Non-English language JP 5 163 124 (attached to JP 5 163 124).
English language JPO Abstract of Non-English language JP 55-22638 (attached to JP 55-22638).

* cited by examiner

*Primary Examiner*—Eisa Elhilo
(74) *Attorney, Agent, or Firm*—Finnegan, Henderson, Farabow, Garrett & Dunner LLP

(57) ABSTRACT

The invention concerns a dyeing composition for keratinous fibres, in particular human keratinous fibres and more particularly hair, comprising a dicationic diazo dye of formula (I), as well as the dyeing composition using same. The invention also concerns the novel compounds of formula (I).

49 Claims, No Drawings

DYEING COMPOSITION FOR KERATINOUS FIBRES COMPRISING A PARTICULAR DICATIONIC DIAZO DYE

The invention relates to a composition for dyeing keratin fibers, in particular human keratin fibres and more particularly the hair, comprising dicationic diazo dye, and also to the process for dyeing keratin fibers using such a composition. The invention also relates to novel dicationic diazo dyes.

It is known practice to dye keratin fibers, and in particular human hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, give rise to colored compounds by a process of oxidative condensation.

It is also known that the shades obtained with these oxidation bases may be varied by combining them with couplers or coloration modifiers, the latter agents being chosen especially from aromatic meta-diamines, meta-aminophenols, meta-diphenols and certain heterocyclic compounds such as indole compounds.

The variety of molecules used as oxidation bases and couplers allows a wide range of colors to be obtained.

This process of oxidation dyeing consists in applying to the keratin fibers oxidation bases or a mixture of oxidation bases and of couplers with an oxidizing agent, for example aqueous hydrogen peroxide solution, leaving the application on the fibers, and then rinsing the fibers. The colorations resulting therefrom are permanent, strong and fast with respect to external agents, especially light, bad weather, washing, perspiration and rubbing. Generally applied at basic pH, dyeing and simultaneous lightening of the fiber may be obtained, which is reflected in practice by the possibility of obtaining a final coloration that is lighter than the original color. In addition, lightening of the fiber may have the advantageous effect of producing a unified color in the case of gray hair, and, in the case of naturally pigmented hair, of bringing out the color, i.e. of making it more visible.

It is also known practice to dye keratin fibers by direct dyeing. The process conventionally used in direct dyeing consists in applying to the keratin fibers direct dyes, which are colored and coloring molecules that have affinity for the fibers, leaving the dyes on the fibers, and then rinsing the fibers.

It is known practice, for example, to use direct dyes belonging to the nitrobenzene, anthraquinone, nitropyridine, azo, indoamine, azine or triarylmethane class.

The colorations resulting therefrom are particularly chromatic colorations, that are temporary or semi-permanent since the nature of the interactions binding the direct dyes to the keratin fiber, and their desorption from the surface and/or the core of the fiber are responsible for their poor dyeing power and their poor resistance to washing or to perspiration. These direct dyes are also generally light-sensitive due to the poor resistance of the chromophore with respect to photochemical attack, leading over time to fading of the coloration of the hair. In addition, their light sensitivity is dependent on their uniform distribution or distribution as aggregates in the keratin fiber.

It is known practice to use direct dyes in combination with oxidizing agents. However, direct dyes are generally sensitive to the action of oxidizing agents such as aqueous hydrogen peroxide solution, and reducing agents such as sodium bisulfite, which makes it generally difficult to use them in compositions for lightening direct dyeing based on aqueous hydrogen peroxide solution and based on a basifying agent or in oxidation dye compositions in combination with precursors such as oxidation bases or couplers.

For example, it has been proposed in patent application FR-1 584 965 to dye the hair with dye compositions based on nitro direct dyes and/or dispersed azo dyes and on ammoniacal aqueous hydrogen peroxide solution, by applying to the hair a mixture of said dyes and of said oxidizing agent, prepared just before use. However, the colorations obtained are found to have insufficient resistance and disappear on shampooing, making the lightening of the hair fiber show through. Such a coloration becomes unattractive by changing over time.

It has also been proposed in patent applications JP-53 95693 and JP-55 022 638 to dye the hair with compositions based on cationic direct dyes of oxazine type and on ammoniacal aqueous hydrogen peroxide solution, by applying to the hair ammoniacal aqueous hydrogen peroxide solution in a first step, followed by a composition based on the oxazine direct dye in a second step. This coloration is unsatisfactory because it requires a process that is made too slow by the leave-in times of the two successive steps. If, besides that, an extemporaneous mixture of the oxazine direct dye with ammoniacal aqueous hydrogen peroxide solution is applied to the hair, the hair fiber is not colored or at most, a virtually nonexistent coloration is obtained.

More recently, patent application FR 2 741 798 has disclosed dye compositions containing direct dyes comprising at least one quaternized nitrogen atom of the azo or azomethine type, said compositions being for extemporaneous mixing at basic pH with an oxidizing composition. These compositions make it possible to obtain uniform, resistant and bright colorations with glints. However, they do not allow keratin fibers to be dyed as strongly as with oxidation dye compositions.

There is thus a real need to find chromatic direct dyes that allow keratin fibers to be dyed as strongly as with oxidation dyes, which are just as stable as oxidation dyes to light, which are also fast with respect to bad weather, washing and perspiration, and which are also stable enough in the presence of oxidizing and reducing agents to be able simultaneously to obtain lightening of the fiber either by using lightening direct compositions containing them, or by using oxidation dye compositions containing them. There is also a real need to find direct dyes that allow keratin fibers to be dyed in a very wide range of colors, in particular very chromatic colors, not forgetting the "fundamental" shades, for instance, blacks and browns.

These aims are achieved with the present invention, one subject of which is a composition for dyeing keratin fibers, and in particular human keratin fibres such as the hair, comprising at least one dicationic diazo dye of formula (I) below:

Formula (I)

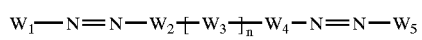

$$W_1-N=N-W_2+W_3+_n W_4-N=N-W_5$$

in which n represents 0 or 1, $W_1$ and $W_5$ independently of each other, represent a heteroaromatic radical of formulae (II) and (III) below:

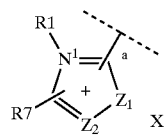

(II)

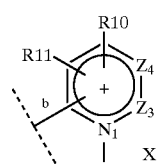

(III)

$W_3$ represents an oxygen atom, a radical $NR_{14}$, a group $-NR_{15}-W_6-NR_{16}-$, a group $-NR_{16}-W_6-O-$, a group $-O-W_6-O-$, a radical $W_6$ or a carbonyl radical, $W_2$ and $W_4$ represent, independently of each other, a carbon-based, pyridine-based or pyridazine-based aromatic group of formula (IV)

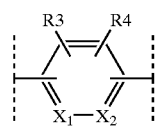

(IV)

$W_6$ represents a 5- or 6-membered aromatic or heteroaromatic group of formula (V):

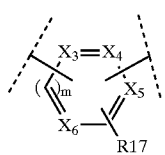

Formula (V)

in which formulae
m represents 0 or 1,
$X_1$ represents a nitrogen atom or a radical $CR_5$,
$X_2$ represents a nitrogen atom or a radical $CR_6$,
$X_3$ represents a nitrogen or carbon atom or a radical $CR_{18}$,
$X_4$ represents a nitrogen or carbon atom or a radical $CR_{19}$,
$X_5$ represents a nitrogen or carbon atom or a radical $CR_{20}$;
$X_6$ represents a nitrogen or carbon atom or a radical $CR_{21}$,
$Z_1$ represents an oxygen or sulfur atom or a radical $NR_8$,
$Z_2$ represents a nitrogen atom or a radical $CR_9$,
$Z_3$ represents a nitrogen atom or a radical $CR_{12}$,
$Z_4$ represents a nitrogen atom or a radical $CR_{13}$,
the bond a of the 5-membered cationic ring of formula (II) is linked to the azo group of formula (I),
the bond b of the 6-membered cationic ring of formula (III) is linked to the azo group of formula (I),
it being understood that when $X_3$ to $X_6$ represent a carbon atom, then they are linked to $W_2$ or $W_4$, it being understood that formula (V) does not contain more than three nitrogen atoms, it being understood that when formula (V) contains three nitrogen atoms, they are noncontiguous, $R_1$, $R_2$ and $R_8$ represent, independently of each other, a linear or branched $C_1-C_8$ alkyl radical optionally substituted with one or more radicals chosen from hydroxyl, $C_2-C_2$ alkoxy, $C_2-C_4$ (poly)hydroxyalkoxy, amino, $C_1-C_2$ (di)alkylamino, carboxyl or sulfonic radicals; a phenyl radical optionally substituted with one or more radicals chosen from hydroxyl, $C_1-C_2$ alkoxy, $C_2-C_4$ (poly)hydroxyalkoxy, amino, $C_1-C_2$ (di) alkylamino, carboxyl or sulfonic radicals; or a halogen atom such as chlorine, fluorine or bromine, $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ represent, independently of each other, a hydrogen atom, a linear or branched $C_1-C_{16}$ hydrocarbon-based chain, which can be saturated or unsaturated, one or more carbon atoms of the carbon-based chain of which may be replaced with an oxygen, nitrogen or sulfur atom or with an $SO_2$ group, and the carbon atoms of which may be substituted, independently of each other, with one or more halogen atoms; $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ not comprising a peroxide bond or diazo or nitroso radicals, $R_7$ with $R_9$, $R_{10}$ with $R_{11}$ and $R_{12}$ with $R_{13}$ may form a carbon-based aromatic ring, such as a phenyl, X is an organic or mineral anion.

According to the invention, when it is indicated that one or more of the carbon atoms of the hydrocarbon-based chain defined for the radicals L, $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{11}$, $R_{19}$, $R_{20}$ and $R_{21}$ may be replaced with an oxygen, nitrogen or sulfur atom or with an $SO_2$ group, and/or when these hydrocarbon-based chains are unsaturated, this means that the following conversions may be performed, for example:

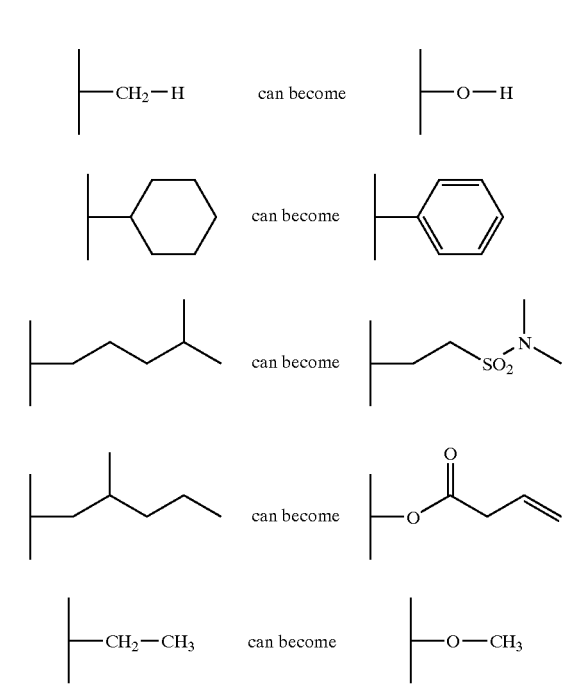

In particular the term "branched hydrocarbon-based chain" means a chain that can form one or more 3- to 6-membered carbon-based rings. The term "unsaturated hydrocarbon-based chain" means a chain that may comprise one or more double bonds and/or one or more triple bonds, this hydrocarbon-based chain possibly leading to aromatic groups.

X is an organic or mineral anion chosen, for example, from a halide such as chloride, bromide, fluoride or iodide; a hydroxide; a sulfate; a hydrogen sulfate; a ($C_1$–$C_6$)alkyl sulfate, for example a methyl sulfate or an ethyl sulfate; an acetate; a tartrate; an oxalate; a ($C_1$–$C_6$)alkylsulfonate such as methylsulfonate; an arylsulfonate that is unsubstituted or substituted with a $C_1$–$C_4$ alkyl radical, for instance a 4-tolylsulfonate.

$R_{14}$, $R_{15}$ and $R_{16}$ preferably represent, independently of each other, a hydrogen atom; a linear or branched $C_1$–$C_6$ alkyl radical, optionally substituted with one or more radicals chosen from hydroxyl, $C_1$–$C_2$ alkoxy, $C_2$–$C_4$ (poly)hydroxyalkoxy, amino, $C_1$–$C_2$ (di)alkylamino, (poly)hydroxyalkylamino, carboxyl and sulfonic radicals; a phenyl radical optionally substituted with one or more radicals chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals or a halogen atom such as chlorine, fluorine or bromine; a $C_1$–$C_4$ alkylsulfonyl radical; an arylsulfonyl radical.

$R_{14}$, $R_{15}$ and $R_{16}$ preferably represent, independently of each other, a hydrogen atom; a linear or branched $C_1$–$C_3$ alkyl radical optionally substituted with one or more radicals chosen from hydroxyl, $C_1$–$C_2$ alkoxy, amino, $C_1$–$C_2$ (di)alkylamino, carboxyl and sulfonic radicals; a phenyl radical optionally substituted with one or more radicals chosen from amino, $C_1$–$C_2$(di)alkylamino and (poly)hydroxyalkylamino radicals.

According to one particularly preferred embodiment, $R_{14}$, $R_{15}$ and $R_{16}$ preferably represent, independently of each other, a hydrogen atom; a linear or branched $C_1$–$C_3$ alkyl radical, which may be substituted with an alkoxy, amino, carboxyl or sulfonyl, such as methyl, ethyl, 2-hydroxyethyl, 2-aminoethyl; 1-carboxymethyl, 2-carboxyethyl, 2-sulfonylethyl, 2-methoxyethyl; a phenyl radical optionally substituted with one or more radicals chosen from amino, $C_1$–$C_2$ (di)alkylamino and (poly)hydroxyalkylamino.

$R_{14}$, $R_{15}$ and $R_{16}$ are preferably chosen from a hydrogen atom; a methyl or 2-hydroxyethyl radical; a phenyl radical optionally substituted with an amino, (di)methylamino or (di)(2-hydroxyethyl)amino radical.

$R_3$, $R_4$, $R_5$, $R_6$, $R_{10}$, $R_{11}$, $R_{12}$, $R_{13}$, $R_{17}$, $R_{18}$, $R_{19}$, $R_{20}$ and $R_{21}$ preferably represent, independently of each other, a hydrogen atom; a linear or branched $C_1$–$C_4$ alkyl radical optionally substituted with one or more radicals chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; a phenyl radical optionally substituted with one or more radicals chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals or a halogen atom such as chlorine, fluorine or bromine; a carboxyl radical; a sulfonylamino radical; a sulfonic radical; a $C_1$–$C_2$ alkoxy radical; a $C_2$–$C_4$ (poly)hydroxyalkoxy radical; an amino radical; a $C_1$–$C_2$ (di)alkylamino radical; a $C_2$–$C_4$ (poly)hydroxyalkylamino radical.

More preferably, $R_3$, $R_4$, $R_5$, $R_6$, $R_{10}$, $R_{11}$, $R_{12}$, $R_{13}$, $R_{17}$, $R_{18}$, $R_{19}$, $R_{20}$ and $R_{21}$ represent a hydrogen atom, a $C_1$–$C_4$ alkyl radical optionally substituted with one or more radicals chosen from hydroxyl, amino and $C_1$–$C_2$ (di)alkylamino radicals; a carboxyl radical; a $C_1$–$C_2$ alkoxy radical; an amino radical; a $C_1$–$C_2$ (di)alkylamino radical; a $C_2$–$C_4$ (poly)hydroxyalkylamino radical.

According to one particularly preferred embodiment, $R_3$, $R_4$, $R_5$, $R_6$, $R_{10}$, $R_{11}$, $R_{12}$, $R_{13}$, $R_{17}$, $R_{18}$, $R_{19}$ $R_{20}$ and $R_{21}$ represent a hydrogen atom, a methyl, phenyl or 2-hydroxymethyl radical, a carboxyl, a methoxy, ethoxy or 2-hydroxyethyloxy radical, or an amino, methylamino, dimethylamino or 2-hydroxyethylamino radical.

According to a particular embodiment, $R_7$ and $R_9$ represent, independently of each other, a hydrogen atom; a linear or branched $C_1$–$C_4$ alkyl radical optionally substituted with one or more radicals chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; a phenyl radical optionally substituted with one or more radicals chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals or a halogen atom such as chlorine, fluorine or bromine; a carboxyl radical; a sulfonylamino radical.

Among these substituents, $R_7$ and $R_9$ preferably represent a hydrogen atom, a phenyl radical or a $C_1$–$C_4$ alkyl radical optionally substituted with one or more radicals chosen from hydroxyl, amino, $C_1$–$C_2$ (di)alkylamino and carboxyl radicals.

According to a preferred embodiment, $R_7$ and $R_9$ preferably represent a hydrogen atom, a methyl, phenyl or 2-hydroxymethyl radical or a carboxyl.

$R_1$, $R_2$ and $R_8$ preferably represent a $C_1$–$C_4$ alkyl radical optionally substituted with one or more radicals chosen from hydroxyl, $C_1$–$C_2$ alkoxy, amino, $C_1$–$C_2$ (di)alkylamino, carboxyl and sulfonic radicals.

According to one particularly preferred embodiment, $R_1$, $R_2$ and $R_8$ preferably represent a methyl, ethyl, 2-hydroxyethyl, 1-carboxymethyl, 2-carboxyethyl or 2-sulfonylethyl radical.

Among the groups of formulae (II) and (III), $W_1$ and $W_5$ preferably represent, independently of each other, an imidazolium, triazolium, thiazolium or pyridinium cationic group.

Among the groups of formula (IV), $W_2$ and $W_4$ preferably represent, independently of each other, a phenyl or pyridyl group.

Among the groups of formula (V), $W_6$ preferably represents a phenyl, pyridyl, triazinyl or pyrimidinyl group.

$W_3$ preferably represents a radical $NR_{14}$, a group $NR_{15}$—$W_6$—$NR_{16}$ or a group $W_6$, in which $R_{14}$, $R_{15}$, $R_{16}$ and $W_6$ are as defined above, in particular according to the preferred modes.

The concentration of dicationic diazo dye of formula (I) may range from 0.001% to 5% by weight approximately, and preferably from about 0.05% to 2% by weight, relative to the total weight of the dye composition.

Among the dicationic diazo dyes of formula (I) according to the present invention, mention may be made especially of the following compounds:

1,3-dimethyl-2-[4-(1,3-dimethyl(imidazol-1-ium)-2-ylazo) phenylamino]phenylazo]imidazol-1-ium, 1,4-dimethyl-3-[4-(1,4-dimethyl(triazol-4-ium)-3-ylazo) phenylamino]phenylazo]triazol-3-ium, 1-methyl-2-[4-(1-methyl(pyridine-1-ium)-2-ylazo)phenylamino]phenylazo]pyridine-1-ium, 1-methyl-3-[4-(1-methyl(pyridine-1-ium)-3-ylazo)-phenylamino]phenylazo]pyridine-1-ium, 1,3-dimethyl-2-[4-(1,3-dimethyl(imidazol-1-ium)-2-ylazo) phenyloxy]phenylazo]imidazol-1-ium, 1,4-dimethyl-3-[4-(1,4-dimethyl(triazol-4-ium)-3-ylazo) phenyloxy]phenylazo]triazol-3-ium, 1-methyl-2-[4-(1-methyl(pyridine-1-ium)-2-ylazo)-phenyloxy]phenylazo]pyridine-1-ium, 1-methyl-3-[4-(1-methyl(pyridine-1-ium)-3-ylazo)-phenyloxy]phenylazo]pyridine-1-ium, 1,3-dimethyl-2-[4-[4-(1,3-dimethyl(imidazol-1-ium)2-ylazo)phenylamino]phenylamino]phenylazo]imidazol-1-ium, 1,4-dimethyl-3-[4-[4-(1,4-dimethyl(triazol-4-ium)$_3$-ylazo)-phenylamino]phenylamino]phenylazo]triazol-3-ium, 1-methyl-2-[4-[4-(1-methyl(pyridine-1-ium)-2-ylazo)-phenylamino]phenylamino]phenylazo]pyridine-1-ium, 1-methyl-3-[4-[4-(1-methyl(pyridine-1-ium)-3-ylazo)-phenylamino]phenylamino]phenylazo]pyridine-1-ium.

Synthesis of the Compounds of the Invention

The methods for obtaining said compounds are based on reactions that are already well known in the literature and disclosed, for example, in the following documents: U.S. Pat. No. 3,291,788, GB-1 186 753, U.S. Pat. No. 3,271,383, EP-0 757 083 and U.S. Pat. No. 5,708,151.

A first synthetic principle consists in starting with a 5- or 6-membered amino heterocycle, such as 2-aminoimidazole, 3-aminotriazole, 2-aminothiazole, 3-aminothiadiazole, 2-aminopyridine or 2-aminopyridazine, which is reacted with sodium nitrite in a polar acidic protic solvent, such as acetic acid or hydrochloric acid, at a temperature generally of between −10° C. and 50° C., in order to generate the corresponding diazonium salt. This salt then reacts with an aromatic derivative of formula (A) or (B) described below, in which $W_3$, $X_1$ and $X_2$ have the meanings described above according to the invention. These aromatic derivatives are obtained by applying the conventional SNAr (aromatic nucleophilic substitution), SN1 (nucleophilic substitution 1) and SN2 (nucleophilic substitution 2) reactions of the literature.

The resulting condensation product then reacts with an alkylating agent such as a dialkyl sulfate or an alkyl halide in a polar solvent and at a temperature of between 0° C. and 150° C. and preferably between 20° C. and 100° C. The 5- or 6-membered heterocyclic part is thus quaternized and the azo compound obtained is cationic.

With a 5-membered heterocycle:

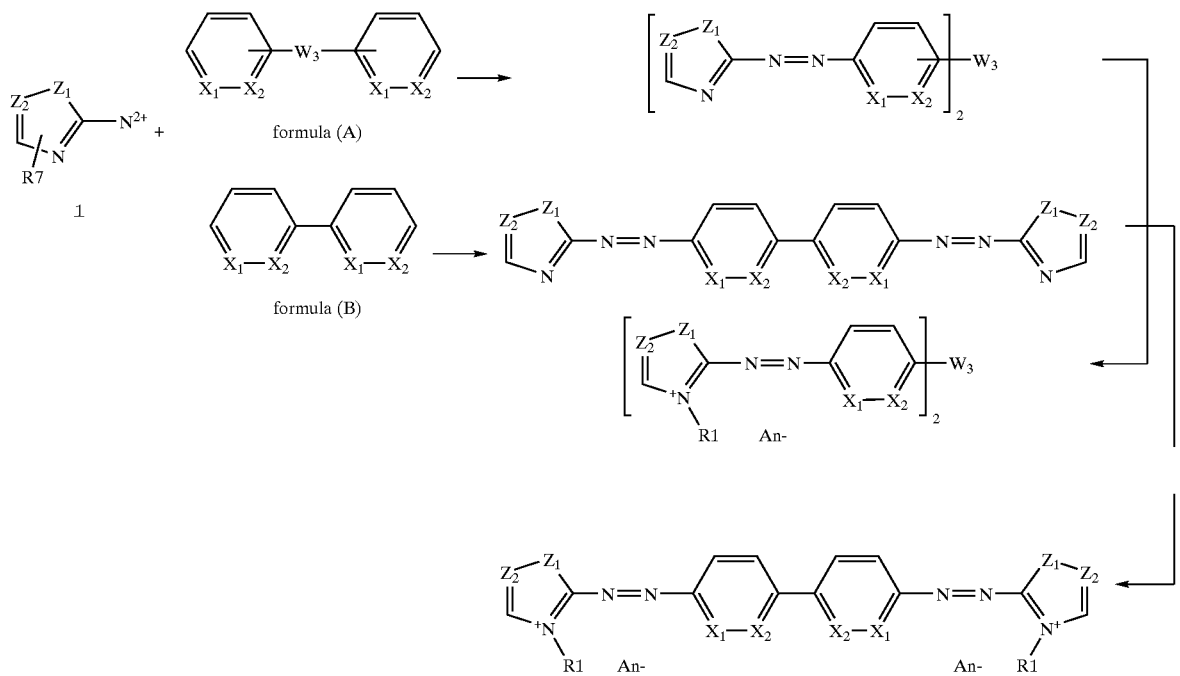

With a 6-membered heterocycle:

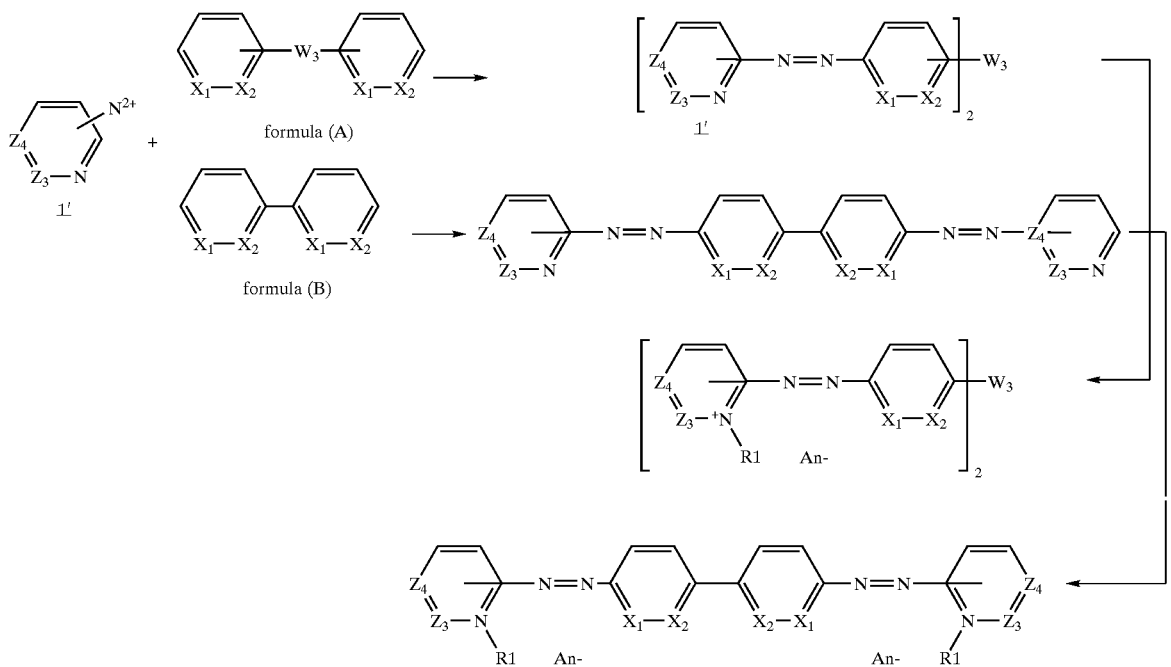

A second synthetic principle consists in reacting a heterocyclic azo compound 2 quaternized on one of the nitrogen atoms of the heterocycle as a 4-methoxyphenylazo series, with an aniline derivative or a heteroaromatic amine 3 in a protic solvent at a temperature of between 25° C. and 150° C. In particular, the quaternary heterocycle may be an imidazolium triazolium, thiazolium, thiadiazolium or oxazolium. The same synthetic principle may be applied in the 6-membered heterocyclic series, such as pyridinium or pyridazinium, giving the compounds of formula 5' from the azo compound 2'.

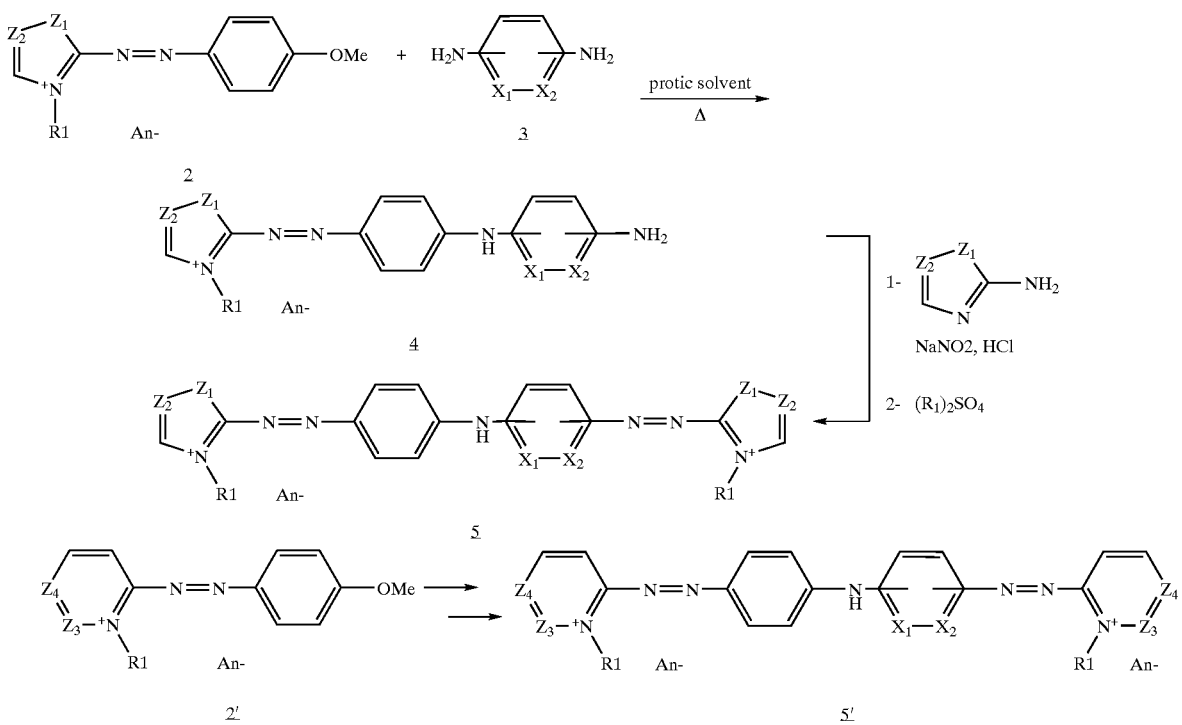

The cationic azo derivative 4 then reacts with a diazonium salt derived from a 5- or 6-membered heterocycle (see above) at a temperature of between −10° C. and 25° C. to give the intermediate monocationic diazo compound, which reacts with an alkylating agent such as a dialkyl sulfate or an alkyl halide in a polar solvent and at a temperature of between 0° C. and 150° C. and preferably between 20° C. and 100° C., to give the dicationic diazo compound 5.

The same synthetic principle may be applied to the 6-membered heterocyclic series, starting with compound 2' to give compound 5'.

In the formulae of the synthesis Scheme, Me denotes a $CH_3$ radical.

The dye composition in accordance with the invention may also contain direct dyes other than those of formula (I), these dyes possibly being chosen especially from neutral, acidic or cationic nitrobenzene direct dyes, neutral, acidic or cationic azo direct dyes, quinone and in particular neutral, acidic or cationic anthraquinone direct dyes, azine direct dyes, methine direct dyes, triarylmethane direct dyes, indoamine direct dyes and natural direct dyes.

Among the benzenic direct dyes that may be used according to the invention, mention may be made, in a nonlimiting manner, of the following compounds:

1,4-diamino-2-nitrobenzene
1-amino-2-nitro-4-(β-hydroxyethylamino)benzene
1-amino-2-nitro-4-bis(β-hydroxyethyl)-aminobenzene
1,4-bis(β-hydroxyethylamino)-2-nitrobenzene
1-β-hydroxyethylamino-2-nitro-4-bis-(β-hydroxyethylamino)benzene
1-β-hydroxyethylamino-2-nitro-4-aminobenzene
1-β-hydroxyethylamino-2-nitro-4-(ethyl)(β-hydroxyethyl)-aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-[tris(hydroxymethyl)methylamino]-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
1-β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-[bis(β-hydroxyethyl)amino]-3-nitrobenzene
1-β-hydroxyethylamino-2-nitrobenzene
1-hydroxy-4-β-hydroxyethylamino-3-nitrobenzene.

Among the azo direct dyes that may be used according to the invention, mention may be made of the cationic azo dyes described in patent applications WO 95/15144, WO 95/01772 and EP 714 954, the content of which forms an integral part of the invention.

Among these compounds, mention may be made most particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate.

Among the azo direct dyes that may also be mentioned are the following dyes described in the Colour Index International 3rd edition:
Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be mentioned are the following dyes:
Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis (β,γ-dihydroxypropylamino) anthraquinone Among the azine dyes that may be mentioned are the following compounds:
Basic Blue 17
Basic Red 2.

Among the triarylmethane dyes that may be used according to the invention, mention may be made of the following compounds:
Basic Green 1
Acid Blue 9
Basic Violet 3
Basic Violet 14
Basic Blue 7
Acid Violet 49

Basic Blue 26

Acid Blue 7

Among the indoamine dyes that may be used according to the invention, mention may be made of the following compounds:

2-β-hydroxyethylamino-5-[bis(β-4'-hydroxyethyl)amino]-anilino-1,4-benzoquinone;

2-β-hydroxyethylamino-5-(2'-methoxy-4'-amino)anilino-1, 4-benzoquinone;

3-N(2'-chloro-4'-hydroxy)phenylacetylamino-6-methoxy-1, 4-benzoquinoneimine;

3-N(3'-chloro-4'-methylamino)phenylureido-6-methyl-1,4-benzoquinoneimine;

3-[4'-N-(ethylcarbamylmethyl)amino]phenylureido-6-methyl-1,4-benzoquinoneimine.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Extracts or decoctions containing these natural dyes may also be used, and especially henna-based poultices or extracts.

The additional direct dye(s) other than those of formula (I) of the present invention preferably represent(s) from 0.001% to 20% by weight approximately, and even more preferably from 0.005% to 10% by weight approximately, relative to the total weight of the product.

The composition of the invention may also comprise an oxidizing agent. This oxidizing agent may be any oxidizing agent conventionally used for bleaching keratin fibers. The oxidizing agent is preferably chosen from hydrogen peroxide, urea peroxide, alkali metal bromates, persalts such as perborates and persulfates, peracids and enzymes, among which mention may be made of peroxidases, 2-electron oxidoreductases such as uricases, and 4-electron oxigenases such as laccases. The use of hydrogen peroxide is particularly preferred.

The composition according to the invention may also comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylene-diamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenylpara-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-amino- toluene, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylamino-phenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives that can be mentioned are the compounds described, for example, in patents DE 2 359 399; JP 88-169 571; JP 05-163 124; EP 0 770 375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]-pyrimidine-3,7-diamine, 2,6-dimethylpyrazolo-[1,5-a]pyrimidine-3,7-diamine, 2,5,N7,N7-tetramethyl-pyrazolo[1,5-a]pyrimidine-3,7-diamine and 3-amino-5-methyl-7-imidazolylpropylaminopyrazolo[1,5-a]pyrimidine, and the addition salts thereof with an acid and the tautomeric forms thereof, when a tautomeric equilibrium exists.

Among the pyrazole derivatives that may be mentioned are the compounds described in patents DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tertbutyl-1-methylpyrazole, 4,5-diamino-1-tertbutyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 0,3,5-diamino-1-methyl-4-methylaminopyrazole and 3,5-diamino-4-(β-hydroxyethyl)amino-1-methylpyrazole, and the addition salts thereof with an acid.

The composition according to the invention may also contain one or more couplers conventionally used for dyeing keratin fibers. Among these couplers, mention may be made especially of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis (β-hydroxy-ethylamino)toluene and the addition salts thereof with an acid.

In the composition of the present invention, the coupler(s) is(are) generally present in an amount ranging from 0.001% to 10% by weight approximately, and more preferably from 0.005% to 6% by weight, relative to the total weight of the dye composition. The oxidation base(s) is(are) present in an amount preferably ranging from 0.001% to 10% by weight approximately, and more preferably from 0.005% to 6% by weight, relative to the total weight of the dye composition.

In general, the addition salts with an acid that may be used in the context of the dye compositions of the invention for the oxidation bases and couplers are chosen especially from the hydrochlorides, hydrobromides, sulfates, citrates, succinates, tartrates, lactates, tosylates, benzenesulfonates, phosphates and acetates.

The medium that is suitable for dyeing, also known as the dye support, generally consists of water or a mixture of water and at least one organic solvent to dissolve the compounds which would not be sufficiently soluble in water. As organic solvent, mention may be made, for example, of $C_1$–$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The organic solvents may be present in proportions ranging preferably from 1% to 40% by weight approximately relative to the total weight of the dye composition, and even more preferably from 5% to 30% by weight approximately.

The dye composition in accordance with the invention can also contain various adjuvants conventionally used in compositions for dyeing the hair, such as anionic, cationic, nonionic, amphoteric or zwitterionic surfactant-s or mixtures thereof, anionic, cationic, nonionic, amphoteric or zwitterionic polymers or mixtures thereof, inorganic or organic thickeners, and in particular anionic, cationic, nonionic or amphoteric associative polymeric thickeners, antioxidants, penetration agents, sequestering agents, fragrances, buffers, dispersing agents, packaging agents such as, for example, silicones, which may or may not be volatile or modified, film-forming agents, ceramides, preserving agents and opacifiers.

The above adjuvants are generally present in an amount for each of them of between 0.01% and 20% by weight relative to the weight of the composition.

Needless to say, a person skilled in the art will take care to select this or these optional additional compounds such that the advantageous properties intrinsically associated with the oxidation dye composition in accordance with the invention are not, or are not substantially, adversely affected by the addition(s) envisaged.

The pH of the dye composition in accordance with the invention is generally between about 3 and 12 and preferably between about 5 and 11. It may be adjusted to the desired value using acidifying or basifying agents usually used in the dyeing of keratin fibers, or alternatively using standard buffer systems.

Among the acidifying agents which may be mentioned, for example, are inorganic or organic acids such as hydrochloric acid, orthophosphoric acid, sulfuric acid, carboxylic acids such as acetic acid, tartaric acid, citric acid and lactic acid, and sulfonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (III) below:

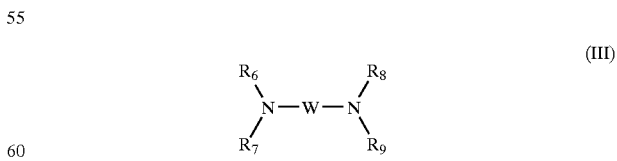

(III)

in which W is a propylene residue which is unsubstituted or substituted with a hydroxyl group or a $C_1$–$C_4$ alkyl radical; $R_6$, $R_7$, $R_8$ and $R_9$, which may be identical or different, represent a hydrogen atom, a $C_1$–$C_4$ alkyl radical or a $C_1$–$C_4$ hydroxyalkyl radical.

The dye composition according to the invention may be in various forms, such as in the form of liquids, creams or gels, or in any other form that is suitable for dyeing keratin fibers, and especially human hair.

A subject of the invention is also a process of direct dyeing, which comprises the application of a dye composition containing a dye of formula (I) as defined above to keratin fibers. After a leave-in time, the keratin fibers are rinsed, revealing colored fibers.

The dye composition containing the cationic azo dye of formula (I) may be applied to the fibers in the presence of an oxidizing agent, which causes bleaching of the fiber (lightening direct dyeing). This oxidizing agent may be added to the composition containing the cationic azo dye at the time of use or directly onto the keratin fiber.

A subject of the invention is also a process of oxidation dyeing, which comprises the application to the fibers of a dye composition comprising a dye of formula (I), at least one oxidation base and optionally at least one coupler, in the presence of an oxidizing agent.

The oxidation base, the coupler and the oxidizing agent are as defined above.

The color may be revealed at acidic, neutral or alkaline pH and the oxidizing agent may be added to the composition of the invention just at the time of use, or it may be introduced using an oxidizing composition containing it, applied to the fibers simultaneously with or sequentially to the dye composition.

In the case of oxidation dyeing or lightening direct dyeing, the dye composition is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibers. After a leave-in time of 3 to 50 minutes approximately and preferably 5 to 30 minutes approximately, the keratin fibers are rinsed, washed with shampoo, rinsed again and then dried.

The oxidizing composition may also contain various adjuvants conventionally used in compositions for dyeing the hair, and as defined above.

The pH of the oxidizing composition containing the oxidizing agent is such that, after mixing with the dye composition, the pH of the resulting composition applied to the keratin fibers preferably ranges from 3 to 12 approximately, and even more preferably between 5 and 11. It may be adjusted to the desired value by means of acidifying or basifying agents usually used in the dyeing of keratin fibers, and as defined above.

The composition that is finally applied to the keratin fibers may be in various forms, such as in the form of liquids, creams or gels or in any other form that is suitable for dyeing keratin fibers, and especially human hair.

Another subject of the invention is a multi-compartment device or dyeing "kit", in which a first compartment contains the dye composition of the invention and a second compartment contains the oxidizing composition. This device may be equipped with a means for applying the desired mixture to the hair, such as the devices described in patent FR-2 586 913 in the name of the Applicant.

Finally, a subject of the invention is also the dicationic diazo dyes of formula (I) as defined above.

The example that follows serves to illustrate the invention without, however, being limiting in nature.

EXAMPLE

This example illustrates the preparation of a compound in accordance with the invention, having the following formula:

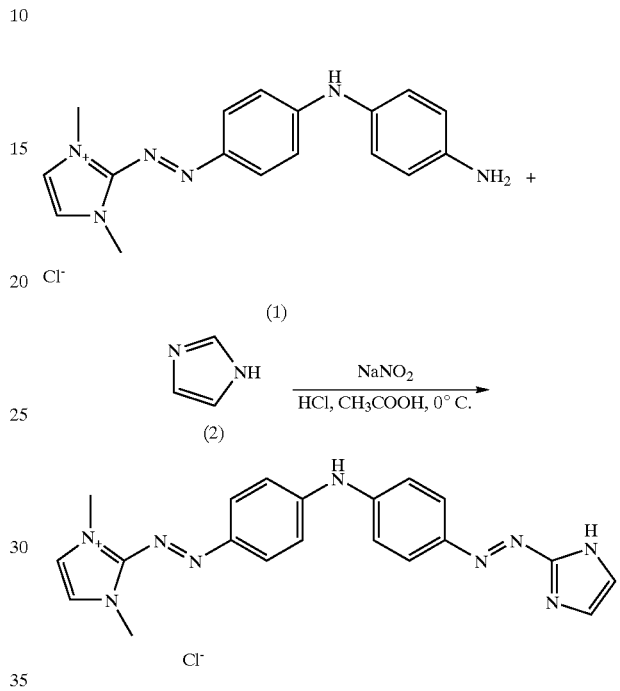

6 g of compound (1), 4.3 ml of 12N hydrochloric acid, 1.9 ml of lactic acid and 11 ml of a mixture consisting of ice and water were placed in a fully equipped round-bottomed flask. The reaction medium was then cooled to 0° C. A solution consisting of 4.3 ml of water and 1.22 g of sodium nitrite was then added dropwise slowly over a period of 20 minutes. The reaction medium was left for one hour at 0° C. with stirring. A solution consisting of 6.4 ml of water and 1.2 g of imidazole was added over 20 minutes. The reaction mixture was then left at room temperature for 2 hours. The pH of the reaction medium was brought to 7.8 with 6N sodium hydroxide solution. The reaction mixture was then filtered through a sinter funnel. The precipitate was washed with methanol. The colored solution was then concentrated and the solid obtained was chromatographed on a column of silica gel (eluent: 9/1/1 MeOH/dichloromethane/buffer mixture). The powder obtained after chromatography was taken up in a few millilitres of water and then dried. After purification, a bright dark-green powder was obtained.

The UV absorption characteristics of this product are as follows:

UV ($H_2O$/MeOH/$AcO^-NH_4^+$) $\lambda_{max}$=538 nm

Analyses:

$^1$H NMR: (400 MHz-MeOD) ppm: 4.07 (s-6H), 7.27 (s-2H); 7.31 (d-2H, J=9 Hz); 7.40 (d-2H, J=8.78 Hz); 7.59 (s-2H); 7.93 (d-2H; J=8.74 Hz); 7.99 (d-2H; J=8.96 Hz)

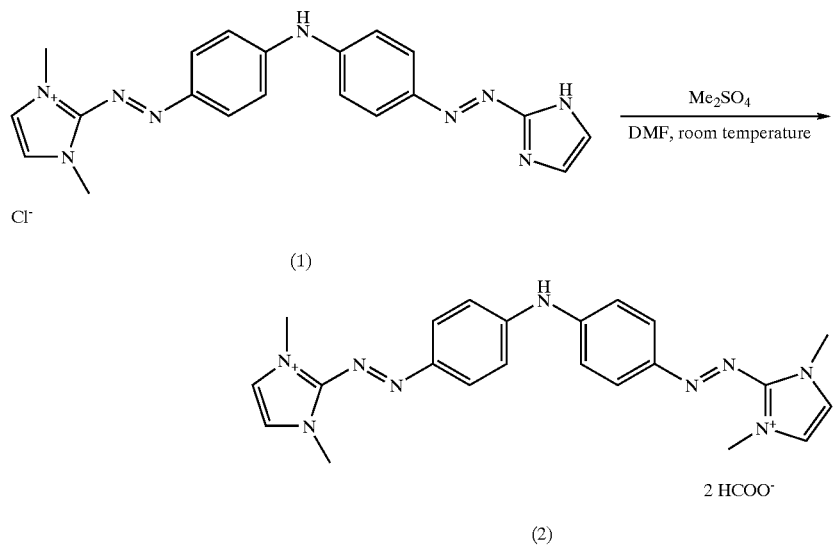

(1)

(2) 2 HCOO⁻

0.094 g of compound (1), 2 ml of DMF and 0.92 ml of dimethyl sulfate were placed in a fully equipped round-bottomed flask at room temperature overnight. The reaction medium was then concentrated under vacuum and the residue was purified by semi-preparative liquid chromatography. After purification, a bright dark-green powder was obtained.

The UV absorption characteristics of this product are as follows:

UV (H$_2$O/MeOH/AcO⁻NH$_4$⁻) $\lambda_{max}$=568 nm

Analyses

1H NMR: (400 MHz-MeOD) ppm: 4.15 (s-9H); 7.52 (d-4H; J=8.96 Hz); 7.72 (s-4H); 8.16 (d-4H, J=8.93 Hz)

The dye obtained dyed hair in a purple shade.

What is claimed is:

1. A composition for dyeing keratin fibers, comprising at least one dicationic diazo dye of formula (I):

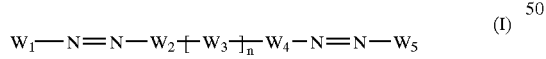

(I)

wherein n is an integer chosen from 0 and 1, $W_1$ and $W_5$, which are identical or different, are chosen from heteroaromatic radicals of formulae (II) and (III):

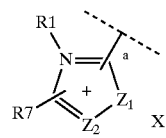

(II)

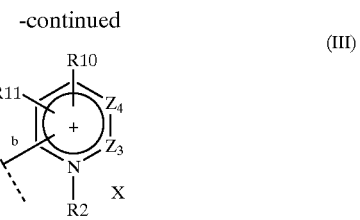

(III)

wherein, $W_3$ is chosen from an oxygen atom, NR$_{14}$, —NR$_{15}$—W$_6$—NR$_{16}$—, —NR$_{16}$—W$_6$—O—, —O—W$_6$—O—, W$_6$ and carbonyl radicals, $W_2$ and $W_4$, which are identical or different, are chosen from carbon-based, pyridine-based and pyridazine-based aromatic groups of formula (IV):

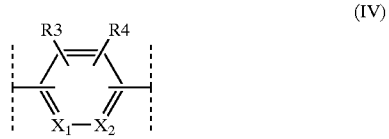

(IV)

$W_6$ is chosen from 5-membered and 6-membered aromatic and heteroaromatic groups of formula (V):

Formula (V)

wherein m is an integer chosen from 0 and 1, $X_1$ is chosen from a nitrogen atom and CR$_5$ radicals, $X_2$ is chosen from a nitrogen atom and CR$_6$ radicals, $X_3$ is chosen from a nitrogen atom, a carbon atom, and $CR_{18}$ radicals, $X_4$ is chosen from a nitrogen atom, a carbon atom, and $CR_{19}$ radicals, $X_5$ is chosen from a nitrogen atom, a carbon atom, and $CR_{20}$ radicals, $X_6$ is chosen from a nitrogen atom, a carbon atom, and $CR_{21}$ radicals, $Z_1$ is chosen from an oxygen atom, a sulfur atom, and $NR_8$ radicals, $Z_2$ is chosen from a nitrogen atom and $CR_9$ radicals, $Z_3$ is chosen from a nitrogen atom and $CR_{12}$ radicals, $Z_4$ is chosen from a nitrogen atom and $CR_{13}$ radicals, the bond a of the 5-membered cationic ring of formula (II) is linked to the azo group of formula (I), the bond b of the 6-membered cationic ring of formula (III) is linked to the azo group of formula (I), with the proviso that when $X_3$ to $X_6$ are chosen from carbon atoms, then they are linked to $W_2$ or $W_4$, and with the proviso that formula (V) does not comprise more than three nitrogen atoms, and further with the proviso that when formula (V) comprises three nitrogen atoms, they are noncontiguous, $R_1$, $R_2$ and $R_8$, which are identical or different, are chosen from linear and branched $C_1$–$C_8$ alkyl radicals optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; and a halogen atom, $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$, which are identical or different, are chosen from a hydrogen atom, linear and branched, saturated and unsaturated $C_1$–$C_{16}$ hydrocarbon-based chains, wherein at least one carbon atom of the hydrocarbon-based chain optionally replaced with at least one group chosen from oxygen, nitrogen and sulfur atoms and with an $SO_2$ group, and wherein the carbon atoms of which may be substituted, independently of each other, with at least one halogen atom; and with the proviso that $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ do not comprise a peroxide bond or diazo or nitroso radicals, $R_7$ with $R_9$, $R_{10}$ with $R_{11}$ and $R_{12}$ with $R_{13}$ may form a carbon-based aromatic ring, and X is chosen from organic and mineral anions.

2. The composition according to claim 1, wherein the keratin fibers are human keratin fibres.

3. The composition according to claim 2, wherein the human keratin fibers are hair.

4. The composition according to claim 1, wherein at least one of $R_7$ with $R_9$, $R_{10}$ with $R_{11}$ and $R_{12}$ with $R_{13}$ form a phenyl group.

5. The composition according to claim 1, wherein $R_{14}$, $R_{15}$ and $R_{16}$, which are identical or different, are chosen from a hydrogen atom; linear and branched $C_1$–$C_6$ alkyl radicals, optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, (poly)hydroxyalkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals, and halogen atoms; $C_1$–$C_4$ alkylsulfonyl radicals; and an arylsulfonyl radical.

6. The composition according to claim 5, wherein the halogen atoms are chosen from chlorine, fluorine and bromine.

7. The composition according to claim 5, wherein $R_{14}$, $R_{15}$ and $R_{16}$, which are identical or different, are chosen from a hydrogen atom; linear and branched $C_1$–$C_3$ alkyl radicals optionally substituted with at least one radical chosen from hydroxyl, $C_1$–$C_2$ alkoxy, amino, $C_1$–$C_2$ (di)alkylamino, carboxyl and sulfonic radicals; phenyl radicals optionally substituted with at least one radical chosen from amino, $C_1$–$C_2$ (di)alkylamino and (poly)hydroxyalkylamino radicals.

8. The composition according to claim 7, wherein $R_{14}$, $R_{15}$ and $R_{16}$, which are identical or different, are chosen from a hydrogen atom; linear and branched $C_1$–$C_3$ alkyl radicals, which are optionally substituted with a radical chosen from alkoxy, amino, carboxyl and sulfonyl radicals; a phenyl radical optionally substituted with at least one radical chosen from amino, $C_1$–$C_2$ (di)alkylamino and (poly)hydroxyalkylamino radicals.

9. The composition according to claim 8, wherein $R_{14}$, $R_{15}$ and $R_{16}$, which are identical or different, are chosen from a hydrogen atom, methyl, ethyl, 2-hydroxyethyl and 2-aminoethyl radicals; 1-carboxymethyl, 2-carboxyethyl, 2-sulfonylethyl and 2-methoxyethyl radicals; a phenyl radical optionally substituted with a group chosen from an amino, (di)methylamino and (di)(2-hydroxyethyl)amino radicals.

10. The composition according to claim 9, wherein $R_{14}$, $R_{15}$ and $R_{16}$, which are identical or different, are chosen from a hydrogen atom; a methyl radical, a 2-hydroxyethyl radical; and a phenyl radical optionally substituted with a radical chosen from amino, (di)methylamino and (di)(2-hydroxyethyl)amino radicals.

11. The composition according to claim 1, wherein $R_3$, $R_4$, $R_5$, $R_6$, $R_{10}$, $R_{11}$, $R_{12}$, $R_{13}$, $R_{17}$, $R_{18}$, $R_{19}$, $R_{20}$ and $R_{21}$, which are identical or different, are chosen from a hydrogen atom; linear and branched $C_1$–$C_4$ alkyl radicals, optionally substituted with at least one radical chosen from hydroxyl, $C_1$–$C_2$ alkoxy, $C_2$–$C_4$(poly)hydroxyalkoxy, amino, $C_1$–$C_2$ (di)alkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals, and a halogen atom; a carboxyl radical; a sulfonylamino radical; a sulfonic radical, $C_1$–$C_2$ alkoxy radicals; $C_2$–$C_4$ (poly)hydroxyalkoxy radicals; an amino radical; $C_1$–$C_2$ (di)alkylamino radicals; and $C_2$–$C_4$ (poly)hydroxyalkylamino radicals.

12. The composition according to claim 11, wherein the halogen atom is chosen from chlorine, fluorine and bromine.

13. The composition according to claim 11, wherein $R_3$, $R_4$, $R_5$, $R_6$, $R_{10}$, $R_{11}$, $R_{12}$, $R_{13}$, $R_{17}$, $R_{18}$, $R_{19}$, $R_{20}$ and $R_{21}$, which are identical or different, are chosen from a hydrogen atom, $C_1$–$C_4$ alkyl radicals optionally substituted with at least one radical chosen from hydroxyl, amino and $C_1$–$C_2$ (di)alkylamino radicals; a carboxyl radical; a $C_1$–$C_2$ alkoxy radical; an amino radical; a $C_1$–$C_2$ (di)alkylamino radical; and $C_2$–$C_4$ (poly)hydroxyalkylamino radicals.

14. The composition according to claim 13, wherein $R_3$, $R_4$, $R_5$, $R_6$, $R_{10}$, $R_{11}$, $R_{12}$, $R_{13}$, $R_{17}$ $R_{18}$, $R_{19}$, $R_{20}$ and $R_{21}$, which are identical or different, are chosen from a hydrogen atom, methyl, phenyl, 2-hydroxymethyl, carboxyl, methoxy, ethoxy, 2-hydroxyethyloxy, an amino, methylamino, dimethylamino, and 2-hydroxyethylamino radicals.

15. The composition according to claim 1, wherein $R_7$ and $R_9$, which are identical or different, are chosen from a hydrogen atom; linear and branched $C_1$–$C_4$ alkyl radicals optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals, and a halogen atom; carboxyl radicals; and sulfonylamino radicals.

16. The composition according to claim 15, wherein $R_7$ and $R_9$, which are identical or different, are chosen from a hydrogen atom, a phenyl radical and $C_1$–$C_4$ alkyl radicals optionally substituted with at least one radical chosen from hydroxyl, amino, $C_1$–$C_2$ (di)alkylamino and carboxyl radicals.

17. The composition according to claim 16, wherein $R_7$ and $R_9$, which are identical or different, are chosen from a hydrogen atom, and methyl, phenyl, 2-hydroxymethyl and carboxyl radicals.

18. The composition according to claim 1, wherein $R_1$, $R_2$ and $R_8$, which are identical or different, are chosen from $C_1$–$C_4$ alkyl radicals optionally substituted with at least one radical chosen from hydroxyl, $C_1$–$C_2$ alkoxy, amino, $C_1$–$C_2$ (di)alkylamino, carboxyl and sulfonic radicals.

19. The composition according to claim 18, wherein $R_1$, $R_2$ and $R_8$, which are identical or different, are chosen from methyl, ethyl, 2-hydroxyethyl, 1-carboxymethyl, 2-carboxyethyl and 2-sulfonylethyl radicals.

20. The composition according to claim 1, wherein $W_1$ and $W_5$, which are identical or different, are chosen from imidazolium, triazolium, thiazolium and pyridinium cationic groups.

21. The composition according to claim 1, wherein $W_2$ and $W_4$, which are identical or different, are chosen from phenyl and pyridyl groups.

22. The composition according to claim 1, wherein $W_6$ is chosen from phenyl, pyridyl, triazinyl and pyrimidinyl groups.

23. The composition according to claim 1, wherein $W_3$ is chosen from a $NR_{14}$ radical, a $NR_{15}$—$W_6$—$NR_{16}$ group, and a $W_6$ group.

24. The composition according to claim 1, wherein the at least one diazo dicationic dye of formula (I) is chosen from:

1,3-dimethyl-2-[4-(1,3-dimethyl(imidazol-1-ium)-2-ylazo)phenylamino]phenylazo]imidazol-1-ium, 1,4-dimethyl-3-[4-(1,4-dimethyl(triazol-4-ium)-3-ylazo)phenylamino]phenylazo]triazol-3-ium, 1-methyl-2-[4-(1-methyl(pyridine-1-ium)-2-ylazo)phenylamino]phenylazo]pyridine-1-ium, 1-methyl-3-[4-(1-methyl(pyridine-1-ium)-3-ylazo)phenylamino]phenylazo]pyridine-1-ium, 1,3-dimethyl-2-[4-(1,3-dimethyl(imidazol-1-ium)-2-ylazo)phenyloxy]phenylazo]imidazol-1-ium, 1,4-dimethyl-3-[4-(1,4-dimethyl(triazol-4-ium)-3-ylazo)phenyloxy]phenylazo]triazol-3-ium, 1-methyl-2-[4-(1-methyl(pyridine-1-ium)-2-ylazo)phenyloxy]phenylazo]pyridine-1-ium, 1-methyl-3-[4-(1-methyl(pyridine-1-ium)-3-ylazo)phenyloxy]phenylazo]pyridine-1-ium, 1,3-dimethyl-2-[4-[4-(1,3-dimethyl(imidazol-1-ium)-2-ylazo)phenylamino]phenylamino]phenylazo]imidazol-1-ium, 1,4-dimethyl-3-[4-[4-(1,3-dimethyl(triazol-4-ium)-3-ylazo)phenylamino]phenylamino]phenylazo]triazol-3-ium, 1-methyl-2-[4-[4-(1-methyl(pyridine-1-ium)-2-ylazo)-phenylamino]phenylamino]phenylazo]pyridine-1-ium, and 1-methyl-3-[4-[4-(1-methyl(pyridine-1-ium)-3-ylazo)-phenylamino]phenylamino]phenylazo]pyridine-1-ium.

25. The composition according to claim 1, wherein the at least one dicationic diazo dye of formula (I) is present in the composition in an amount ranging from 0.001% to 5% by weight, relative to the total weight of the composition.

26. The composition according to claim 25, wherein the at least one dicationic diazo dye of formula (I) is present in the composition in an amount ranging from 0.05% to 2% by weight, relative to the total weight of the composition.

27. The composition according to claim 1, further comprising at least one oxidation base.

28. The composition according to claim 27, wherein the at least one oxidation base is chosen from para-phenylenediamines, bis(phenyl)alkylenediamines, para-aminophenols, ortho-aminophenols, heterocyclic bases, and the addition salts thereof with an acid.

29. The composition according to claim 27, wherein the at least one oxidation base is present in the composition in an amount ranging from 0.001% to 10%, by weight, relative to the total weight of the composition.

30. The composition according to claim 29, wherein the at least one oxidation base is present in the composition in an amount ranging from 0.005% to 6% by weight, relative to the total weight of the composition.

31. The composition according to claim 1, further comprising at least one coupler.

32. The composition according to claim 31, wherein the at least one coupler is chosen from meta-phenylenediamines, meta-aminophenols, meta-diphenols, naphthalene-based couplers, heterocyclic couplers, and the addition salts thereof with an acid.

33. The composition according to claim 1, further comprising at least one direct dye other than those of formula (I), chosen from neutral, acidic and cationic nitrobenzene direct dyes; neutral, acidic and cationic azo direct dyes; quinone direct dyes, azine direct dyes, methine direct dyes, triarylmethane direct dyes, indoamine direct dyes and natural direct dyes.

34. The composition according to claim 33, wherein the quinone direct dye is chosen from neutral, acidic and cationic anthraquinone direct dyes.

35. The composition according to claim 1, further comprising an oxidizing agent.

36. The composition according to claim 35, wherein the oxidizing agent is hydrogen peroxide.

37. A process for dyeing keratin fibers, comprising applying to the keratin fibers a composition comprising, at least one dicationic diazo dye of formula (I):

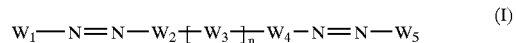

wherein n is an integer chosen from 0 and 1, $W_1$ and $W_5$, which are identical or different, are chosen from heteroaromatic radicals of formulae (II) and (III):

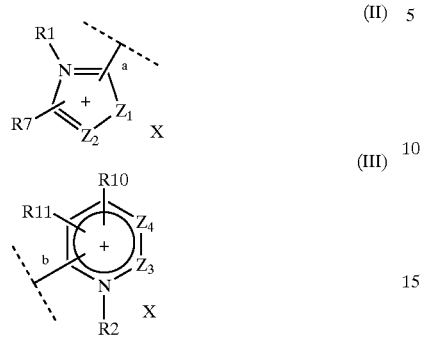

wherein,
$W_3$ is chosen from an oxygen atom, $NR_{14}$, $-NR_{15}-W_6-NR_{16}-$, $-NR_{16}-W_6-O-$, $-O-W_6-O-$,
$W_6$ and carbonyl radicals,
$W_2$ and $W_4$, which are identical or different, are chosen from carbon-based, pyridine-based and pyridazine-based aromatic groups of formula (IV):

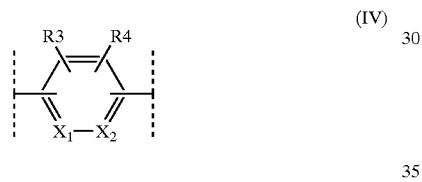

$W_6$ is chosen from 5-membered and 6-membered aromatic and heteroaromatic groups of formula (V):

wherein
m is an integer chosen from 0 and 1,
$X_1$ is chosen from a nitrogen atom and $CR_5$ radicals,
$X_2$ is chosen from a nitrogen atom and $CR_6$ radicals,
$X_3$ is chosen from a nitrogen atom, a carbon atom, and $CR_{18}$ radicals,
$X_4$ is chosen from a nitrogen atom, a carbon atom, and $CR_{19}$ radicals,
$X_5$ is chosen from a nitrogen atom, a carbon atom, and $CR_{20}$ radicals,
$X_6$ is chosen from a nitrogen atom, a carbon atom, and $CR_{21}$ radicals,
$Z_1$ is chosen from an oxygen atom, a sulfur atom, and $NR_8$ radicals,
$Z_2$ is chosen from a nitrogen atom and $CR_9$ radicals,
$Z_3$ is chosen from a nitrogen atom and $CR_{12}$ radicals,
$Z_4$ is chosen from a nitrogen atom and $CR_{13}$ radicals,
the bond a of the 5-membered cationic ring of formula (II) is linked to the azo group of formula (I), the bond b of the 6-membered cationic ring of formula (III) is linked to the azo group of formula (I),
with the proviso that when $X_3$ to $X_6$ are chosen from carbon atoms, then they are linked to $W_2$ or $W_4$,
and with the proviso that formula (V) does not comprise more than three nitrogen atoms,
and further with the proviso that when formula (V) comprises three nitrogen atoms, they are noncontiguous,
$R_1$, $R_2$ and $R_8$, which are identical or different, are chosen from linear and branched $C_1-C_8$ alkyl radicals optionally substituted with at least one radical chosen from hydroxyl, $C_1-C_2$ alkoxy, $C_2-C_4$ (poly)hydroxyalkoxy, amino, $C_1-C_2$ (di) alkylamino, carboxyl and sulfonic radicals; a phenyl radical optionally substituted with at least one radical chosen from hydroxyl, $C_1-C_2$ alkoxy, $C_2-C_4$ (poly)hydroxyalkoxy, amino, $C_1-C_2$ (di) alkylamino, carboxyl and sulfonic radicals; and a halogen atom,
$R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$, which are identical or different, are chosen from a hydrogen atom, linear and branched, saturated and unsaturated $C_1-C_{16}$ hydrocarbon-based chains, wherein at least one carbon atom of the carbon-based chain may be replaced with at least one atom chosen from oxygen, nitrogen and sulfur atoms and with an $SO_2$ group, and wherein the carbon atoms of which may be substituted, independently of each other, with at least one halogen atom; and with the proviso that $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ do not comprise a peroxide bond or diazo or nitroso radicals,
$R_7$ with $R_9$, $R_{10}$ with $R_{11}$ and $R_{12}$ with $R_{13}$ may form a carbon-based aromatic ring, and
X is chosen from organic and mineral anions.

38. The process according to claim 37, wherein the keratin fibers are human keratin fibers.

39. The process according to claim 38, wherein the human keratin fibers are hair.

40. The process according to claim 37, wherein the dye composition further comprises at least one oxidizing agent.

41. The process according to claim 40, wherein the at least one oxidizing agent is mixed with the dye composition at the time of use.

42. The process according to claims 40, when the at least one oxidizing agent is applied to the fibers in the form of an oxidizing composition simultaneously with, or sequentially to, the dye composition.

43. A process for the oxidation dyeing of keratin fibers, comprising applying to the keratin fibers at least one dye composition comprising at least one dicationic diazo dye of formula (I):

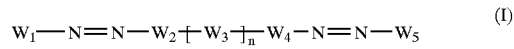

wherein
n is an integer chosen from 0 and 1, $W_1$ and $W_5$, which are identical or different, are chosen from heteroaromatic radicals of formulae (II) and (III):

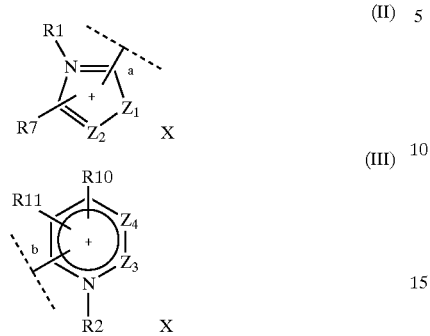

wherein, $W_3$ is chosen from an oxygen atom, $NR_{14}$, $-NR_{15}-W_6-NR_{16}-$, $-NR_{16}-W_6-O-$, $-O-W_6-O-$, $W_6$ and carbonyl radicals, $W_2$ and $W_4$, which are identical or different, are chosen from carbon based, pyridine based and pyridazine-based aromatic groups of formula (IV):

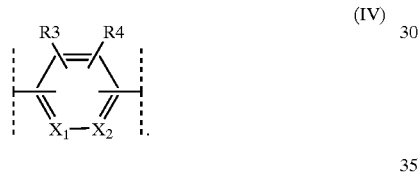

$W_6$ is chosen from 5-membered and 6-membered aromatic and heteroaromatic groups of formula (V):

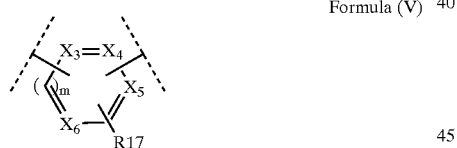

Formula (V)

wherein m is an integer chosen from 0 and 1, $X_1$ is chosen from a nitrogen atom and $CR_5$ radicals, $X_2$ is chosen from a nitrogen atom and $CR_6$ radicals, $X_3$ is chosen from a nitrogen atom, a carbon atom, and $CR_{18}$ radicals, $X_4$ is chosen from a nitrogen atom, a carbon atom, and $C_{19}$ radicals, $X_5$ is chosen from a nitrogen atom, a carbon atom, and $CR_{20}$ radicals, $X_6$ is chosen from a nitrogen atom, a carbon atom, and $CR_{21}$ radicals, $Z_1$ is chosen from an oxygen atom, a sulfur atom, and $NR_8$ radicals, $Z_2$ is chosen from a nitrogen atom and $CR_9$ radicals, $Z_3$ is chosen from a nitrogen atom and $CR_{12}$ radicals, $Z_4$ is chosen from a nitrogen atom and $CR_{13}$ radicals, the bond a of the 5-membered cationic ring of formula (II) is linked to the azo group of formula (I), the bond b of the 6-membered cationic ring of formula (III) is linked to the azo group of formula (I), with the proviso that when $X_3$ to $X_6$ are chosen from carbon atoms, then they are linked to $W_2$ or $W_4$, and with the proviso that formula (V) does not comprise more than three nitrogen atoms, and further with the proviso that when formula (V) comprises three nitrogen atoms, they are noncontiguous, $R_1$, $R_2$ and $R_8$, which are identical or different, are chosen from linear and branched $C_1$–$C_8$ alkyl radicals optionally substituted with at least one radical chosen from hydroxyl, $C_1$–$C_2$ alkoxy, $C_2$–$C_4$ (poly) hydroxyalkoxy, amino, $C_1$–$C_2$ (di)alkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; and a halogen atom, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$, which are identical or different, are chosen from a hydrogen atom, linear and branched, saturated and unsaturated $C_1$–$C_{16}$ hydrocarbon-based chains, wherein at least one carbon atom of the carbon-based chain may be replaced with at least one atom chosen from oxygen, nitrogen and sulfur atoms and with an $SO_2$ group, and wherein the carbon atoms of which may be substituted, independently of each other, with at least one halogen atom; and with the proviso that $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ do not comprise a peroxide bond or diazo or nitroso radicals, $R_7$ with $R_9$, $R_{10}$ with $R_{11}$ and $R_{12}$ with $R_{13}$ may form a carbon-based aromatic ring, and X is chosen from organic and mineral anions, and also comprising at least one oxidation base and optionally at least one coupler, wherein the application to the fibers is in the presence of an oxidizing agent.

44. The process according to claim 43, wherein the keratin fibers are human keratin fibers.

45. The process according to claim 44, wherein the human keratin fibers are hair.

46. The process according to claim 43, wherein the oxidizing agent is mixed with the dye composition at the time of use.

47. The process according to claim 43, wherein the oxidizing agent is applied to the fibers in the form of an oxidizing composition simultaneously with, or sequentially to, the dye composition.

48. A multi-compartment dyeing kit, wherein at least one first compartment comprises a composition comprising at least one dicationic diazo dye of formula (I):

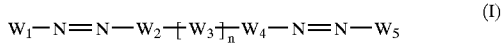

wherein n is an integer chosen from 0 and 1, $W_1$ and $W_5$, which are identical or different, are chosen from heteroaromatic radicals of formulae (II) and (III):

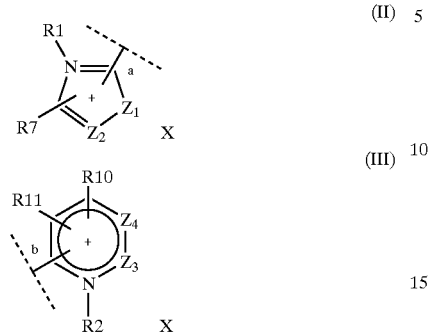

wherein,
$W_3$ is chosen from an oxygen atom, $NR_{14}$, $—NR_{15}—W_6—NR_{16}—$, $—NR_{16}—W_6—O—$, $—O—W_6—O—$,
$W_6$ and carbonyl radicals,
$W_2$ and $W_4$, which are identical or different, are chosen from carbon-based, pyridine-based and pyridazine-based aromatic groups of formula (IV):

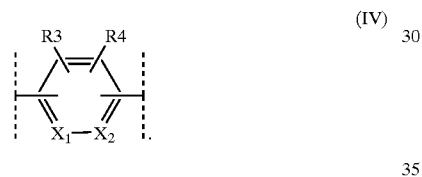

$W_6$ is chosen from 5-membered and 6-membered aromatic and heteroaromatic groups of formula (V):

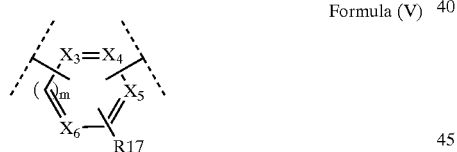

Formula (V)

wherein
m is an integer chosen from 0 and 1,
$X_1$ is chosen from a nitrogen atom and $CR_5$ radicals,
$X_2$ is chosen from a nitrogen atom and $CR_6$ radicals,
$X_3$ is chosen from a nitrogen atom, a carbon atom, and $CR_{18}$ radicals,
$X_4$ is chosen from a nitrogen atom, a carbon atom, and $CR_{19}$ radicals,
$X_5$ is chosen from a nitrogen atom, a carbon atom, and $CR_{20}$ radicals,
$Z_1$ is chosen from an oxygen atom, a sulfur atom, and $NR_8$ radicals,
$Z_2$ is chosen from a nitrogen atom and $CR_9$ radicals,
$Z_3$ is chosen from a nitrogen atom and $CR_{12}$ radicals,
$Z_4$ is chosen from a nitrogen atom and $CR_{13}$ radicals,
the bond a of the 5-membered cationic ring of formula (II) is linked to the azo group of formula (I),
the bond b of the 6-membered cationic ring of formula (III) is linked to the azo group of formula (I),
with the proviso that when $X_3$ to $X_6$ are chosen from carbon atoms, then they are linked to $W_2$ or $W_4$,
and with the proviso that formula (V) does not comprise more than three nitrogen atoms,
and further with the proviso that when formula (V) comprises three nitrogen atoms, they are noncontiguous,
$R_1$, $R_2$ and $R_8$, which are identical or different, are chosen from linear and branched $C_1$–$C_8$ alkyl radicals optionally substituted with at least one radical chosen from hydroxyl, $C_1$–$C_2$ alkoxy, $C_2$–$C_4$ (poly) hydroxyalkoxy, amino, $C_1$–$C_2$ (di)alkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; and a halogen atom,
$R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$, which are identical or different, are chosen from a hydrogen atom, linear and branched, saturated and unsaturated $C_1$–$C_{16}$ hydrocarbon-based chains, wherein at least one carbon atom of the carbon-based chain may be replaced with at least one atom chosen from oxygen, nitrogen and sulfur atoms and with an $SO_2$ group, and wherein the carbon atoms of which may be substituted, independently of each other, with at least one halogen atom; and with the proviso that $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$ do not comprise a peroxide bond or diazo or nitroso radicals,
$R_7$ with $R_9$, $R_{10}$ with $R_{11}$ and $R_{12}$ with $R_{13}$ may form a carbon-based aromatic ring, and
X is chosen from organic and mineral anions, and at least one second compartment comprises an oxidizing composition.

49. A dicationic diazo compound of formula (I):

wherein
n is an integer chosen from 0 and 1,
$W_1$ and $W_5$, which are identical or different, are chosen from heteroaromatic radicals of formulae (II) and (III):

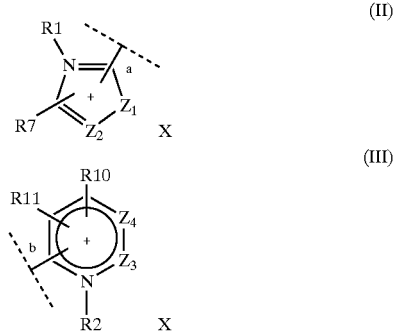

wherein,
$W_3$ is chosen from an oxygen atom, $NR_{14}$, $—NR_{15}—W_6—NR_{16}—$, $—NR_6—W_6—O—$, $—O—W_6—O—$, $W_6$ and carbonyl radicals, $W_2$ and $W_4$, which are identical or different, are chosen from carbon-based, pyridine-based and pyridazine-based aromatic groups of formula (IV):

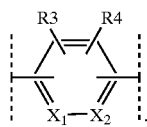

(IV)

$W_6$ is chosen from 5-membered and 6-membered aromatic and heteroaromatic groups of formula (V):

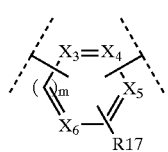

Formula (V)

wherein m is an integer chosen from 0 and 1, $X_1$ is chosen from a nitrogen atom and $CR_5$ radicals, $X_2$ is chosen from a nitrogen atom and $CR_6$ radicals, $X_3$ is chosen from a nitrogen atom, a carbon atom, and $CR_{18}$ radicals, $X_4$ is chosen from a nitrogen atom, a carbon atom, and $CR_{19}$ radicals, $X_5$ is chosen from a nitrogen atom, a carbon atom, and $CR_{20}$ radicals, $X_6$ is chosen from a nitrogen atom, a carbon atom, and $CR_{21}$, radicals, $Z_1$ is chosen from an oxygen atom, a sulfur atom, and $NR_8$ radicals, $Z_2$ is chosen from a nitrogen atom and $CR_9$ radicals, $Z_3$ is chosen from a nitrogen atom and $CR_{12}$ radicals, $Z_4$ is chosen from a nitrogen atom and $CR_{13}$ radicals, the bond a of the 5-membered cationic ring of formula (II) is linked to the azo group of formula (I), the bond b of the 6-membered cationic ring of formula (III) is linked to the azo group of formula (I), with the proviso that when $X_3$ to $X_6$ are chosen from carbon atoms, then they are linked to $W_2$ or $W_4$, and with the proviso that formula (V) does not comprise more than three nitrogen atoms, and further with the proviso that when formula (V) comprises three nitrogen atoms, they are noncontiguous, $R_1$, $R_2$ and $R_8$, which are identical or different, are chosen from linear and branched $C_1$–$C_6$ alkyl radicals optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; a phenyl radical optionally substituted with at least one radical chosen from hydroxyl, $C_1$–$C_2$ alkoxy, $C_2$–$C_4$ (poly)hydroxyalkoxy, amino, $C_1$–$C_2$ (di)alkylamino, carboxyl and sulfonic radicals; and a halogen atom, $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$ and $R_{21}$, which are identical or different, are chosen from a hydrogen atom, linear and branched, saturated and unsaturated $C_1$–$C_{16}$ hydrocarbon-based chains, wherein at least one carbon atom of the carbon-based chain may be replaced with at least one atom chosen from oxygen, nitrogen and sulfur atoms and with an $SO_2$ group, and wherein the carbon atoms of which may be substituted, independently of each other, with at least one halogen atom; and with the proviso that $R_3$, $R_4$, $R_5$, $R_6$, $R_7$, $R_9$, $R_{10}$, $R_{11}$, $R_{12}$, $R_{13}$, $R_{14}$, $R_{15}$, $R_{16}$, $R_{17}$, $R_{17}$, $R_{19}$, $R_{20}$ and $R_{21}$ do not comprise a peroxide bond or diazo or nitroso radicals, $R_7$ with $R_9$, $R_{10}$ with $R_{11}$, and $R_{12}$ with $R_{13}$ may form a carbon-based aromatic ring, and X is chosen from organic and mineral anions.

* * * * *

UNITED STATES PATENT AND TRADEMARK OFFICE
CERTIFICATE OF CORRECTION

PATENT NO. : 7,001,436 B2
APPLICATION NO. : 10/480202
DATED : February 21, 2006
INVENTOR(S) : Vidal et al.

It is certified that error appears in the above-identified patent and that said Letters Patent is hereby corrected as shown below:

In claim 1, column 20, line 56, "Formula (V)" should read --(V)--.

In claim 1, column 21, line 8, "$CR_2$, radicals," should read --$CR_{21}$ radicals,--.

In claim 14, column 22, line 63, "$R_{17} R_{18}$," should read --$R_{17}$, $R_{18}$,--.

In claim 37, column 25, line 40, "Formula (V)" should read --(V)--.

In claim 42, column 26, line 52, "claims 40," should read --claim 40,--.

In claim 42, column 26, line 52, "when" should read --wherein--.

In claim 43, column 27, line 25, "carbon based, pyridine based" should read --carbon-based, pyridine-based--.

In claim 43, column 27, line 40, "Formula (V)" should read --(V)--.

In claim 43, column 27, line 55, "$C_{19}$" should read --$CR_{19}$--.

In claim 43, column 28, line 23, after "$R_7$,", delete "$R_8$,".

In claim 48, column 29, line 40, "Formula (V)" should read --(V)--.

UNITED STATES PATENT AND TRADEMARK OFFICE
CERTIFICATE OF CORRECTION

PATENT NO. : 7,001,436 B2
APPLICATION NO. : 10/480202
DATED : February 21, 2006
INVENTOR(S) : Vidal et al.

It is certified that error appears in the above-identified patent and that said Letters Patent is hereby corrected as shown below:

In claim 48, column 29, line 57, after "$CR_{20}$ radicals,", insert the line
--$X_6$ is chosen from a nitrogen atom, a carbon atom, and $CR_{21}$ radicals,--.

In claim 48, column 30, line 18, after "$R_7$,", delete "$R_8$,".

In claim 49, column 31, line 18, "Formula (V)" should read --(V)--.

In claim 49, column 31, line 36, "$CR_{21}$, radicals," should read --$CR_{21}$ radicals,--.

In claim 49, column 32, line 14, "$C_1$-$C_6$ alkyl" should read --$C_1$-$C_8$ alkyl--.

In claim 49, column 32, line 34, "$R_{17}$, $R_{17}$," should read --$R_{17}$, $R_{18}$,--.

Signed and Sealed this

Eighteenth Day of July, 2006

JON W. DUDAS
*Director of the United States Patent and Trademark Office*